United States Patent [19]

Fujisawa et al.

[11] 4,266,067

[45] May 5, 1981

[54] PROCESS FOR PREPARING THIOPHENE DERIVATIVES

[75] Inventors: Tamotsu Fujisawa; Kiyoshi Kondo; Kunikazu Sakai, all of Yamato, Japan

[73] Assignee: Sagami Chemical Research Center, Tokyo, Japan

[21] Appl. No.: 110,331

[22] Filed: Jan. 7, 1980

Related U.S. Application Data

[63] Continuation of Ser. No. 886,639, Mar. 15, 1978, abandoned.

[30] Foreign Application Priority Data

Mar. 18, 1977 [JP] Japan .................................. 52-29175
Mar. 18, 1977 [JP] Japan .................................. 52-29176
Mar. 18, 1977 [JP] Japan .................................. 52-56427

[51] Int. Cl.$^3$ ............................................. C07D 333/24
[52] U.S. Cl. ........................................................ 549/79
[58] Field of Search ........................................... 549/79

[56] References Cited

U.S. PATENT DOCUMENTS 3,013,079 12/1961 Pearson .................................. 549/78

OTHER PUBLICATIONS

Reeve, JACS, 83, 2755 (1961).
Kieboom, Chem. Abst., 74, 99173.
Brunswig, Berichte, 19, pp. 2890–2896, (1886).

*Primary Examiner*—Alan Siegel
*Attorney, Agent, or Firm*—Frishauf, Holtz, Goodman & Woodward

[57] ABSTRACT

Process for the preparation of a series of thiophene derivatives, from which 2-thiopheneacetic acid derivatives can easily be prepared, in high yields and selectivity by using substituted or unsubstituted 2-acetylthiophenes as the starting materials by easy operations. 2-Thiopheneacetic acid derivatives are very useful compounds as the chemical modifier of penicillin and cephalosporin. In the course of the reaction, 2-(dihaloacetyl)thiophenes are formed which are valuable intermediates for the production of not only 2-thiopheneacetic acids but also thioprofenic acid which is known as an anti-inflammatory agent.

10 Claims, No Drawings

PROCESS FOR PREPARING THIOPHENE DERIVATIVES

This is a continuation of application Ser. No. 886,639, filed Mar. 15, 1978, now abandoned.

BACKGROUND OF THE INVENTION

1. Field of the Invention

The present invention relates to a process for preparing thiophene derivatives and in more detail, this invention relates to a process for preparing a series of thiophene derivatives, from which 2-thiopheneacetic acid derivatives can easily be prepared, in high yields and selectivity by using substituted or unsubstituted 2-acetylthiophenes, which are easily available from thiophenes, as the starting materials by easy operations.

2. Description of the Prior Art

The processes for the preparation of α-substituted 2-thiopheneacetic acid derivatives having the general formula

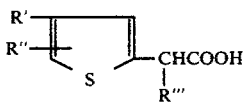

(wherein R' and R" are independently selected from hydrogen, halogen atom or lower alkyl group and R''' is alkoxyl group, hydroxyl group or amino group) heretofore known to the art are: (1) the condensation of a 2-thiophenealdehyde with bromoform in the presence of a base (J. Amer. Chem. Soc., 83, 2755 (1961)), (2) the oxidation of a 2-acetylthiophene with selenium dioxide and then treating with an alkali (Arkiv Kemi., 11, 519 (1957)), (3), the preparation of 2-thiophenealdehyde cyanohydrin and then conducting hydrolysis (Japanese Patent Disclosure No. 8775/73), (4) the addition of glyoxylic acid on thiophene (Japanese Patent Disclosure No. 49954/74), etc.

However, the process (1) necessitates the use of expensive bromoform and 2-thiophenealdehyde as the raw materials and the yield of the product is low. The process (2) necessitates the use of expensive and dangerous selenium dioxide and is difficult to adopt as a commercial process. The process (3) requires 2-thiophenealdehyde which is difficultly accessible, commercially and necessitates the use of highly poisonous hydrogen cyanide. Although the process (4) requires a shorter reaction step, yield of the product is low and is thus difficult to adopt as a commercial process.

Further, the process for the preparation of 2-thiopheneglycolic acid by the reduction of 2-thiopheneglyoxylic acid in an alcohol by the use of sodium amalgam was known prior to the invention (F. Ernst, Ber., 19, 3278 (1886), however, commercial production by the process above is difficult, since all of the synthetic methods give 2-thiopheneglyoxylic acid in low yield, which is required as the starting material.

It was known that the α-substituted 2-thiopheneacetic acid derivatives themselves can be converted to penicillin derivatives having antibiotical activities by reacting them with penicillanic acid derivatives (Cf. e.g. Netherlands Octrooiaanvrage No. 6506584), and 2-thiopheneacetic acids which are the compounds obtainable by replacing the substituent located in α-position of said α-substituted 2-thiopheneacetic acids with hydrogen are very useful as chemical modifier of penicillin and cephalosporin (Cf. J. Amer. Chem. Soc., 84, 3401 (1962)) and various methods for the preparation of 2-thiopheneacetic acids have heretofore been known (Senda, Yuki Gosei Kagaku Kyokai-shi (J. Synth. Org. Chem. Japan), 34, 779 (1976)), and as to the process for the preparation of 2-thiopheneacetic acids by reduction of a 2-thiopheneglycolic acid, the known process is a method by heating 2-thiopheneglycolic acid with hydrogen iodide and phosphorous (F. Ernst, Ber., 19, 3278 (1886)). However, no yield is given in the above literature, and repetition of the experiment conducted by us according to the literature procedure gave practically no 2-thiopheneacetic acid, and therefore, this process can be difficultly adoptable as a commercial process.

The main processes for the preparation of 2-thiopheneacetic acid heretofore known may be classified into three processes described below, according to the starting materials employed: (1) converting 2-chloromethylthiophene to 2-cyanomethylthiophene at first by treating with an alkali cyanide, and then conducting hydrolysis thereof (Japanese Patent Disclosure No. 46063/77); (2) converting by Willgerodt reaction of 2-acetylthiophene with ammonium polysulfide to 2-thiopheneacetamide at first and then conducting hydrolysis thereof (Otto Dann, Ger. No. P. 832755 (1952)); (3) (a) acting potassium cyanide and an ester of chloroformic acid on 2-thiophenealdehyde to form an α-alkoxycarbonyloxy-2-thiopheneacetonitrile, and then conducting catalytic hydrogenation thereof to 2-cyanomethylthiophene, and further conducting hydrolysis thereof (M. J. Soulal, M. C. Woodford, B. P. No. 1,122,658 (1968); (b) treating the condensation product of 2-thiophenealdehyde and methyl methylthiomethyl sulfoxide with hydrogen chloride in alcohol to form an ester of 2-thiopheneacetic acid and then conducting hydrolysis thereof (Japanese Patent Disclosure No. 46063/77); etc. However, the process (1) includes difficulties in that 2-chloromethylthiophene is difficult to handle because it is unstable, and is a lachrymatory substance, and also, highly poisonous bis(chloromethyl) ether is formed as by-product during the preparation of this compound. The process (2) possesses its shortcomings in that it requires a high-temperature and high-pressure condition in performing Willgerodt reaction, and requires severe conditions for the hydrolysis. Also, the process (3) (a) has its demerit in that it necessitates the use of highly poisonous cyanide compounds, and requires many reaction stages, etc. The process (3) (b) is disadvantageous in that it needs attention in handling, and produces sulfur compounds having a strong unpleasant odor.

SUMMARY OF THE INVENTION

Accordingly, the object of this invention is to provide a process for preparing a series of thiophene derivatives, from which 2-thiopheneacetic acid derivatives can easily be prepared, in a high yield by using substituted or unsubstituted 2-acetylthiophenes, which are readily obtainable from thiophenes, as the starting material by easy operations.

To assist the understanding of this invention, the process and products of the invention are given in a chemical scheme:

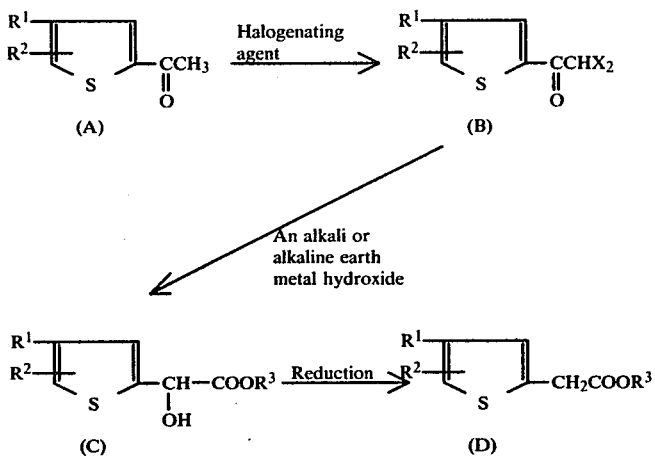

In the scheme shown above, $R^1$ and $R^2$ are independently selected from the group consisting of hydrogen, halogens, alkyl groups and aroyl groups; $R^3$ represents hydrogen or alkyl group; and X represents halogen atom and preferably one selected from the group consisting of chlorine, bromine and iodine.

In the scheme shown above, compounds (B) are useful not only as an intermediate of the synthesis of the final product (D) of the process of this invention but also as an intermediate of the synthesis of thioprofenic acid which is known as an anti-inflammatory agent.

In this invention, the process to prepare compounds (C) via compounds (B) from compounds (A) which can easily be prepared by well known acetylation process from thiophenes, is developed by the inventors through intensive studies to establish a process which overcomes the disadvantages found in the prior art aforementioned and selectively affords only the desired compounds, and discovered that the desired compounds can be prepared in a good yield by using a 2-acetylthiophene as a starting material which is easily obtainable as an industrial raw material through markets.

That is, the object of this invention is to provide a process for preparing 2-thiopheneglycolic acid derivatives (C) having the general formula

(C)

which comprises reacting a 2-acetylthiophene (A) represented by the general formula

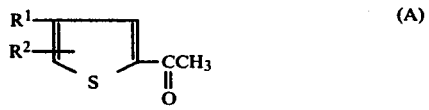

(A)

with a halogenating agent to obtain 2-dihaloacetylthiophenes (B) having the general formula

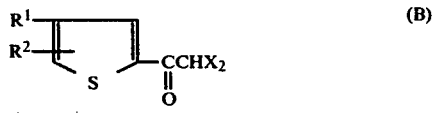

(B)

at first, and then treating the reaction product thus obtained with an alkali or alkaline earth metal hydroxide and if desired, the reaction product is further esterified in any suitable manner known in the art, e.g. reacting with an alcohol shown by the general formula $R^3OH$ (wherein $R^1$, $R^2$, $R^3$ and X are as aforedescribed).

The compounds (C) thus obtained can easily be converted to compounds (D), i.e. 2-thiopheneacetic acids which are final product of the process of this invention by reduction.

That is, the second object of this invention is to provide a process for reducing the compounds (C) to provide compounds (D).

Other object of this invention will become apparent during the following detailed description of the invention.

DETAILED DESCRIPTION OF THE INVENTION

The process of this invention requires reacting a 2-acetylthiophene with a halogenating agent to obtain compounds (B) as an indispensable procedure in the first step.

As examples of the 2-acetylthiophenes represented by the general formula (A) which are used as the starting materials of this step, 2-acetylthiophene, 2-acetylthiophenes having a lower alkyl group such as methyl group, ethyl group, n-propyl group, isopropyl group, n-butyl group, isobutyl group, sec-butyl group, t-butyl group, etc. at the 3-, 4- or 5-position, 2-acetylthiophenes substituted by chlorine, bromine or iodine at the 4- or 5-position, 2-acetylthiophenes substituted by a halogen and a lower alkyl group at the 3- and 4-positions, 3- and 5-positions or 4-and 5-positions, 5-aroyl-2-acetylthiophenes such as 5-benzoyl-2-acetylthiophene, etc. may be cited. These 2-acetylthiophenes may be prepared readily and in high yield from the corresponding thiophenes by acetylation at the 2-position by the use of acetyl chloride or acetic anhydride in the presence of a Lewis acid or a proton acid. If desired, they may be prepared by introducing various alkyl groups, halogen atoms and aroyl groups onto 2-acetylthiophene. Also, as examples of the halogenating agent which is the other starting material, chlorine, bromine, sulfuryl chloride, sulfuryl bromide, t-butyl hypochlorite, selenium oxychloride, N-chlorosuccinimide, N-bromosuccinimide, etc. may be cited, but the use of chlorine and bromine is recommended as economical industrial starting materials.

In the practice of this process, use of a solvent is preferred, and many types of solvents, e.g. a halogenated hydrocarbon such as carbon tetrachloride, methylene chloride, chloroform, etc. or a polar solvent such as an aliphatic carboxylic acid including acetic acid, propionic acid, butyric acid, etc., may be used. The use of an aliphatic carboxylic acid is particularly preferred in order to minimize the formation of by-products such as the formation of products having a halogenated thiophene ring, a monohaloacetylated product, a trihaloacetylated product, etc.

The reaction can be performed at a temperature range of from 0° C. to the boiling point of the solvent used, but a temperature of from 0° C. to 50° C. is preferred to avoid the formation of the by-products such as those described above. The desired 2-(dihaloacetyl)thiophene can be prepared in high yields by performing the present process under the conditions described above.

Then, the 2-(dihaloacetyl)thiophene represented by the general formula (B) thus obtained is treated with an alkali or an alkaline earth metal hydroxide. As to the hydroxide, the use of sodium hydroxide or potassium hydroxide is preferred from an economical as well as an industrial view-point. It is preferable to use 4 molar equivalents of these hydroxides to compound (B), and generally, the desired compounds can be prepared selectively by the use of 3 to 6 molar equivalents of the hydroxides. In the practice of the reaction, heating is required to initiate the reaction, but heating at around 50° C. is sufficient, and the reaction proceeds with evolution of heat. The desired compounds (C) can be prepared in high yields and in a practically pure form by performing this step under the conditions described above.

Further, the 2-thiopheneglycolic acid derivatives (C) prepared in accordance with the process described above can be readily converted to 2-thiopheneacetic acid derivatives (D) by reductive treatment.

One of the preferred reduction process is catalytically hydrogenating a 2-thiopheneglycolic acid derivative represented by the general formula

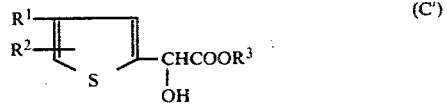 (C')

(wherein, $R^1$, $R^2$ and $R^3$ are as defined before) in the presence of a platinum group metal or a supported platinum group metal catalyst.

It is known that the double bond and the carbon-sulfur bond of a thiophene ring are generally susceptible to reduction, and it gives rise to various products, and that thiophenes poison catalysts. Accordingly, processes for hydrogenation by the use of catalysts which would overcome such difficulties were investigated by the inventors, and it was found that catalysts containing a platinum group metal and a platinum group metal which is supported on a carrier can give good results, and that palladium black and supported palladium are highly active and their use is preferred. As examples of carriers, carbon, calcium carbonate, barium sulfate, barium carbonate, asbestos, etc. may be cited.

In the practice of this process, it is preferred to perform the reaction under a hydrogen atmosphere, by adding a catalyst to 2-thiopheneglycolic acids or the esters thereof per se or to its solution. Alcohols such as methanol and ethanol can be used as the solvent. This reaction may be performed at a temperature ranging from room temperature to 150° C., but a temperature between 50° and 80° C. is preferable in view of the reaction rate and selectivity. The reaction can be conducted under a high pressure, but atmospheric pressure is desirable to avoid the leakage of hydrogen from the reaction vessel. It is sufficient to use 0.1–10% by weight of a palladium catalyst to the acids, but use of 1–3% by weight is preferred.

DESCRIPTIONS OF THE PREFERRED EMBODIMENTS

In the followings, the invention will be explained in more detailed and material fashion by illustration of Examples, however, it is to be noted that these Examples are given only for the purpose of illustration and are not to be construed as limiting this invention thereto. Incidentally, in this specification, the abbreviations of "sh" and "br" are used to show "shoulder" and "broad", respectively, and the other abbreviations are used in the conventional manner. As the internal standard used in NMR measurement, tetramethylsilane was used in all cases and the values were shown by δ, in ppm.

EXAMPLE 1

2-Acetylthiophene (6.31 g, 50.0 mmol) was dissolved in glacial acetic acid (25 ml) and chlorine gas was introduced to the reaction system under water cooling. The cooling water was so adjusted that the temperature of the reaction system was kept below 28° C. After passing chlorine for ca. 2 hr., the reaction was completed and the reaction solution showed a pale yellow coloration. At this point, the introduction of chlorine was stopped, the reaction solution was poured onto 150 ml of crushed ice, and was extracted with diethylether. The ether layer was washed with cold water and dried with sodium sulfate. Removal of the ether under a reduced pressure gave 9.8 g of 2-(dichloroacetyl)thiophene as an oily substance. The value 9.8 g is the quantitative yield.
bp: 79°–82° C./0.15 mmHg.
NMR (CCl4): 6.24 (s, 1H), 7.13 (dd, J=5.2 Hz, J=3.9 Hz, 1H), 7.73 (dd, J=5.2 Hz, J=1.0 Hz, 1H) and 7.97 (dd, J=3.9 Hz, J=1.0 Hz, 1H).
IR (liquid film, KBr plate): 3090, 1692, 1682 (sh), 1675 (sh), 1515, 1413, 805, 727 and 716 (cm$^{-1}$).
MS (70 eV) (m/e); 196 (below 1%), 194 (below 1%), 111 (100%) and 83 (10%).

EXAMPLE 2

The reaction was performed in the same manner as in Example 1 except that the reaction was carried out at room temperature by the use of carbon tetrachloride as the solvent instead of acetic acid, giving 3.7 g of 2-(dichloroacetyl)thiophene (yield: 39%).

EXAMPLE 3

The reaction was conducted in the same manner as in Example 1 except that the reaction was carried out at 47° C. using carbon tetrachloride as the solvent instead of acetic acid, gave 4.0 g of 2-(dichloroacetyl)thiophene (yield: 41%).

EXAMPLE 4

To an aqueous solution of 10.0 g (250 mmol) of sodium hydroxide kept at 50° C., 9.8 g (50 mmol) of 2-(dichloroacetyl)thiophene was added in dropwise with vigorous stirring. The temperature of the reaction mixture rose to 55° C. by the heat of the reaction, and the rate of the addition was so adjusted that the temperature did not rise above the temperature. The addition of 2-(dichloroacetyl)thiophene described above required ca. 2 hr., and after the addition, stirring was continued for another 1 hr. at the same temperature. The reaction mixture was cooled to room temperature, washed with diethylether to remove neutral substances, and then made acidic (pH ca. 1) by addition of 12 N hydrochloric acid to the aqueous solution under ice cooling. The aqueous solution was extracted three times with diethylether (100 ml), and the ether layer was washed with a saturated aqueous solution of sodium chloride, and then dried with sodium sulfate. Removal of the extraction solvent under a reduced pressure gave 7.9 g of 2-thiopheneglycolic acid. The value 7.9 g is the quantitative yield.

mp: 75° C. (recrystallization from benzene).

NMR (CDCl$_3$): 5.42 (s, 1H), 6.7–7.4 (m, 3H) and 8.17 (br. s, 2H).

IR (KBr disc): 3380, 3500–2500 (broad), 1725, 1528, 1430, 1278, 1050 and 703 (cm$^{-1}$).

MS (70 eV) (m/e): 158 (4.1%) (M+), 156 (4.6%), 113 (37.3%), 111 (100%) and 97 (77.9%).

EXAMPLE 5

The reaction was performed in the same manner as in Example 4 except that a solution of 8.0 g (200 mmol) of sodium hydroxide in 90 ml of water was used and 14.2 g (50 mmol) of 2-(dibromoacetyl)thiophene was used, gave 5.6 g of 2-thiopheneglycolic acid (yield: 77%).

EXAMPLE 6

Chlorine was bubbled through a solution of 6.31 g (50 mmol) of 2-acetylthiophene in glacial acetic acid (25 ml). The reaction solution which evolved heat was cooled with water and kept below 28° C. The reaction was discontinued at the stage when the reaction solution turned slight yellow by the excess chlorine, and then acetic acid was distilled off at room temperature under a reduced pressure to give crude 2-(dichloroacetyl)thiophene. This crude product was added in dropwise with vigorous stirring to a solution of 10.0 g (250 mmol) of sodium hydroxide in water (90 ml) which was kept at 50° C. The temperature of the reaction solution rose to ca. 55° C. The addition was completed after ca. 2 hr., and the mixture was stirred for another 1 hr. at the same temperature. After cooling to room temperature, the reaction mixture was washed with diethylether, then acidified (pH 1) by addition of 12 N hydrochloric acid under ice cooling. The acidic material which separated out was extracted with diethylether, and the ether layer was washed with a saturated aqueous solution of sodium chloride, and after drying with sodium sulfate, the solvent was distilled off to give 2-thiopheneglycolic acid in quantitative yield (7.9 g).

EXAMPLE 7

To a solution of 6.30 g (50 mmol) of 2-acetylthiophene in carbon disulfide (40 ml), 16.0 g (100 mmol) of bromine was added in dropwise under ice cooling. Carbon disulfide was then distilled off under a reduced pressure at room temperature to give crude 2-(dibromoacetyl)thiophene. This crude product was treated with an aqueous alkaline solution in the same manner as in Example 6 to give 2-thiopheneglycolic acid in 63% yield (5.0 g).

EXAMPLE 8

A mixture of 421 mg of 2-thiopheneglycolic acid and 40 mg of 30% palladium-asbestos catalyst in 2.7 ml of methanol was heated under reflux with stirring under a hydrogen atmosphere at a normal pressure. After 15 hr., the catalyst was filtered off and methanol was then distilled off under a reduced pressure to give 127 mg of 2-thiopheneacetic acid and 283 mg of unreacted 2-thiopheneglycolic acid. The conversion of 2-thiopheneglycolic acid was 33% and the selectivity to 2-thiopheneacetic acid was 100%.

NMR (CDCl$_3$): 3.91 (s, 2H), 7.30 (d, J=3 Hz, 2H), 7.31 (t, J=3 Hz, 1H), and 11.12 (s, 1H).

We claim:

1. A process for the preparation of 2-thiopheneglycolic acid of the formula:

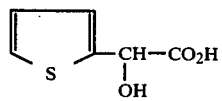

which comprises reacting 2-acetylthiophene of the formula

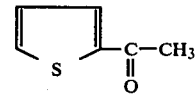

with chlorine in glacial acetic acid to produce a 2-(dichloroacetyl)thiophene of the formula

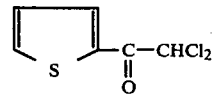

and reacting said 2-(dichloroacetyl)thiophene with an alkali or an alkaline earth metal hydroxide to produce 2-thiopheneglycolic acid.

2. The process of claim 1, wherein said reaction of 2-acetylthiophene with chlorine is carried out at a temperature of from 0° to 50° C.

3. The process of claim 1, wherein said hydroxide is sodium hydroxide or potassium hydroxide in a ratio of between 3 and 6 moles of said hydroxide per mole of the 2-(dichloroacetyl)thiophene.

4. The process of claim 3, wherein the ratio of said hydroxide to said 2-(dichloroacetyl)thiophene is about 4:1.

5. A process for the preparation of a 2-thiopheneacetic acid of the formula

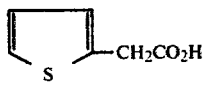

which comprises reacting 2-acetylthiophene of the formula

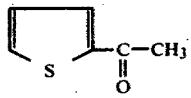

with chlorine in glacial acetic acid to produce a 2-(dichloroacetyl)thiophene of the formula

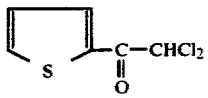

reacting said 2-(dichloroacetyl)thiophene with an alkali or an alkaline earth metal hydroxide to produce 2-thiopheneglycolic acid having the formula

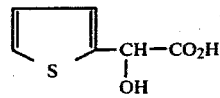

and then catalytically hydrogenating said 2-thiopheneglycolic acid under a hydrogen atmosphere in the presence of a platinum group metal catalyst to produce 2-thiopheneacetic acid.

6. The process of claim 5, wherein said hydrogenation catalyst is supported on a carrier.

7. The process of claim 5, wherein said hydrogenation catalyst is not supported on a carrier.

8. The process of claim 5, wherein said hydrogenation catalyst is palladium black.

9. The process of claim 5, wherein said hydrogenation is carried out in an aliphatic alcohol solvent.

10. The process of claim 5, wherein said hydrogenation is carried out within a range of from room temperature to 150° C.

* * * * *

UNITED STATES PATENT AND TRADEMARK OFFICE
CERTIFICATE OF CORRECTION

PATENT NO. :  4,266,067
DATED      :  May 5, 1981
INVENTOR(S):  TAMOTSU FUJISAWA et al

It is certified that error appears in the above—identified patent and that said Letters Patent is hereby corrected as shown below:

Title Page, left column, under the heading "FOREIGN
    APPLICATION PRIORITY DATA", the third line under
    said heading should read
  --May 18, 1977  [JP]  Japan................52-56427--.

*Signed and Sealed this*

*Twenty-seventh* Day of *October 1981*

[SEAL]

Attest:

GERALD J. MOSSINGHOFF

*Attesting Officer*     *Commissioner of Patents and Trademarks*